(12) United States Patent
Kajimoto et al.

(10) Patent No.: US 7,163,399 B2
(45) Date of Patent: Jan. 16, 2007

(54) ULTRASONIC THERAPY DEVICE FOR DENTAL IMPLANT AND THERAPY METHOD THEREFOR

(75) Inventors: Naoko Kajimoto, Motosu-gun (JP); Atsumi Ohta, Tokyo (JP); Nobuo Ogiwara, Ageo (JP)

(73) Assignees: Bio Map Co., Ltd., Tokyo (JP); Ito Co., Ltd., Tokyo (JP)

( * ) Notice: Subject to any disclaimer, the term of this patent is extended or adjusted under 35 U.S.C. 154(b) by 295 days.

(21) Appl. No.: 10/372,070

(22) Filed: Feb. 21, 2003

(65) Prior Publication Data

US 2004/0063073 A1   Apr. 1, 2004

(30) Foreign Application Priority Data

Sep. 27, 2002   (JP)   ............................. 2002-283769

(51) Int. Cl.
 *A61C 5/00*   (2006.01)
(52) U.S. Cl. ...................................................... 433/215
(58) Field of Classification Search ................ 433/215, 433/173, 174, 29; 601/2, 1; 600/439
See application file for complete search history.

(56) References Cited

U.S. PATENT DOCUMENTS 4,244,373 A  *  1/1981  Nachman ........................ 607/9
5,496,256 A  *  3/1996  Bock et al. ..................... 601/2
5,738,521 A  *  4/1998  Dugot .......................... 433/173

FOREIGN PATENT DOCUMENTS

| JP | 52-51260 | 12/1977 |
| JP | 04-024028 | 1/1992 |
| JP | 07-096042 | 4/1995 |
| JP | 11-033069 | 2/1999 |
| JP | 2001-231788 | 8/2001 |

* cited by examiner

*Primary Examiner*—Melba Bumgarner
(74) *Attorney, Agent, or Firm*—Bell, Boyd & Lloyd LLC (57) ABSTRACT

An ultrasonic therapy device comprises two bodies and two holding members. The body, at the inner face of which an oscillator is embedded, covers an affected area into which implant fixtures are embedded. The holding member which holds the body has a shape of a crown which covers teeth next to the affected area. Two teeth were removed from the affected area into which two implant fixtures are embedded. Each of the bodies covers the affected area between the teeth which is covered by the holding members so that the bodies are exactly fixed in an oral cavity. In this state, it is possible to accelerate osteogenesis around the implant fixtures by supplying an ultrasonic signal from an external driver to the oscillator.

6 Claims, 7 Drawing Sheets

ULTRASONIC THERAPY DEVICE FOR DENTAL IMPLANT AND THERAPY METHOD THEREFOR

BACKGROUND OF THE INVENTION

1. Field of the Invention

The Invention relates to an ultrasonic therapy device and to a therapy method utilizing the ultrasonic therapy device for dental therapy when using an implant fixture.

2. Background Art

A conventional method for dental implant therapy comprises a first step of embedding an artificial root having the shape of a pin, a so-called implant fixture, into a maxilla or a mandibula, and a second step of fixing a crown onto the artificial root by using a screw which is formed in the upper face of the artificial root. In this method, the period for the embedded artificial root to be integrated osseous tissue due to spontaneous growth is necessary between the first step and the second step. It is therefore necessary to use a temporary denture, and therefore, it is inconvenient for the patient to use the temporary denture. No positive therapy method or therapy device for accelerating the integration of the artificial root with the osseous tissue is utilized.

Physical therapies for accelerating the integration have a potential to accelerate the integration. However, specific structures of an device which hold an ultrasonic oscillator so as to emit ultrasonic waves to an affected area are not known, and therefore, it is not possible to hold the ultrasonic oscillator to the affective area.

The present invention is made in view of the above inconveniences and seeks to provide devices for holding the ultrasonic oscillator and also to provide a therapy method using the devices.

SUMMARY OF THE INVENTION

In an aspect of the present invention is, an ultrasonic therapy device is provided comprising an oscillator which is arranged in a vicinity of an affected area in an oral cavity where an implant fixture is embedded and which outputs ultrasonic waves to the affected area.

Another aspect of the present invention is to provide at least one body which is arranged in the vicinity of the affected area where the implant fixture is embedded, an oscillator which is arranged at an inner face of the body, and a pair of holding members which is arranged at side faces of the body and cover a tooth next to the affected area.

Another aspect of the present invention is to provide at least one body which is arranged in the vicinity of the affected area where the implant fixture is embedded, an oscillator which is arranged at an inner face of the body, and a pair of engaging members which is arranged at side faces of the body and elastically engage with a tooth next to the affected area Another aspect of the present invention is to provide at least one body which is arranged in the vicinity of the affected area where an implant fixture is embedded, an oscillator which is arranged at an inner face of the body, and a mounting member on which the body is mounted and which is arranged so as to cover all teeth in a maxilla or a mandibula.

Another aspect of the present invention is to provide at least one body which is arranged in the vicinity of the affected area where an implant fixture is embedded, the oscillator which is arranged an inner face of the body, a headgear which a patient has on its head, an elastic member which elastically holds said oscillator in the vicinity of said affected area.

Another aspect of the present invention is to provide an ultrasonic therapy device according to the first aspect of the present invention, comprising not less than one body which is arranged in the vicinity of the affected area where an implant fixture is embedded, a supporting member comprising a concavity having a shape relative to a shape conforming a shape conforming uneven area in the mouth of the patient.

Another aspect of the present invention is to provide an ultrasonic therapy device wherein an oscillator is arranged in a bead member in which dentures are arranged and which is held in a human oral cavity.

Another aspect of the therapy method of the present Invention is to embed an implant fixture in a patient and also to output ultrasonic waves to the patient into which the implant fixture is embedded.

Another aspect of the therapy method is to output ultrasonic waves by a oscillator which is supported in the organism by various kinds of supporting equipment.

The present invention can be utilized for implant therapies in oral cavities in which some teeth or all teeth are missing, and because the oscillator emits ultrasonic waves in a state in which the body of the ultrasonic therapy device is securely supported by the organism, it is possible to accelerate ossification for integrating an implant fixture with an osseous tissue so that the time necessary for the implant therapy will be minimized.

DESCRIPTION OF THE PREFERRED EMBODIMENTS

Figure 1A:
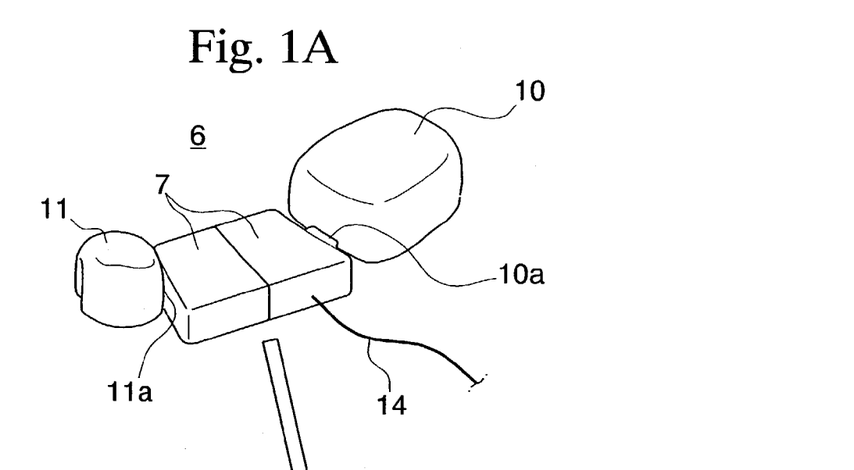
FIG. 1A is a perspective view of the first embodiment of the ultrasonic therapy device of the present Invention.
Figure 1B:
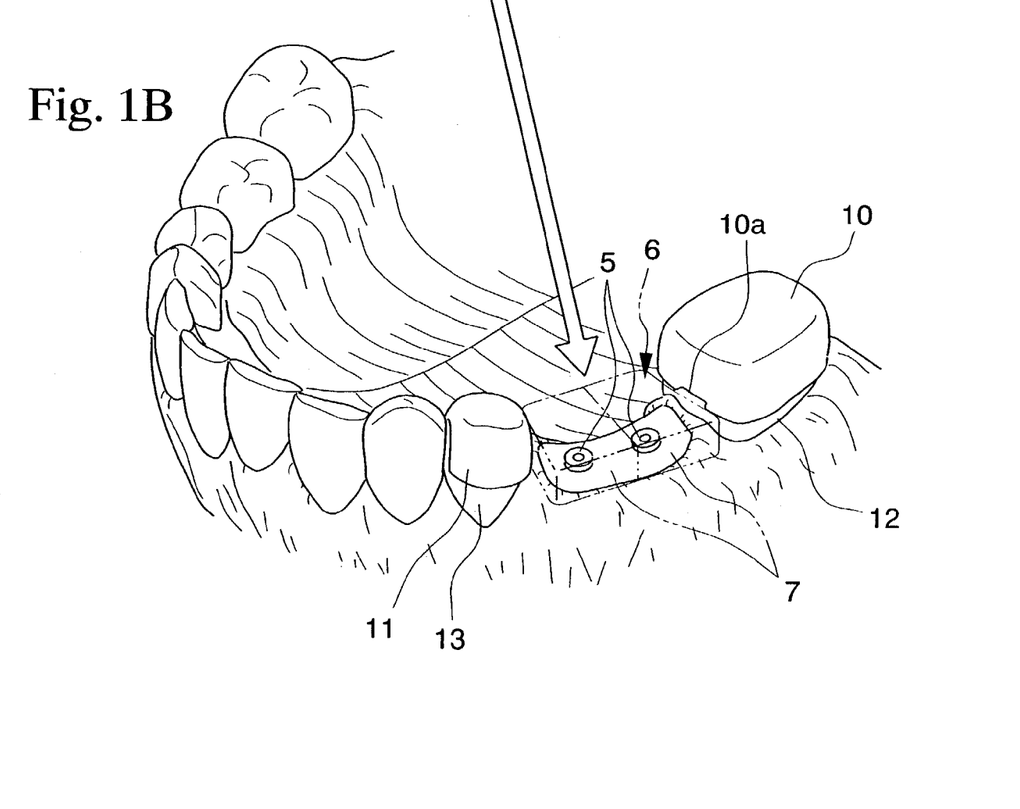
FIG. 1B is a perspective view of the first embodiment of the ultrasonic therapy device in a state in which the device is placed at an affected portion.
Figure 2:
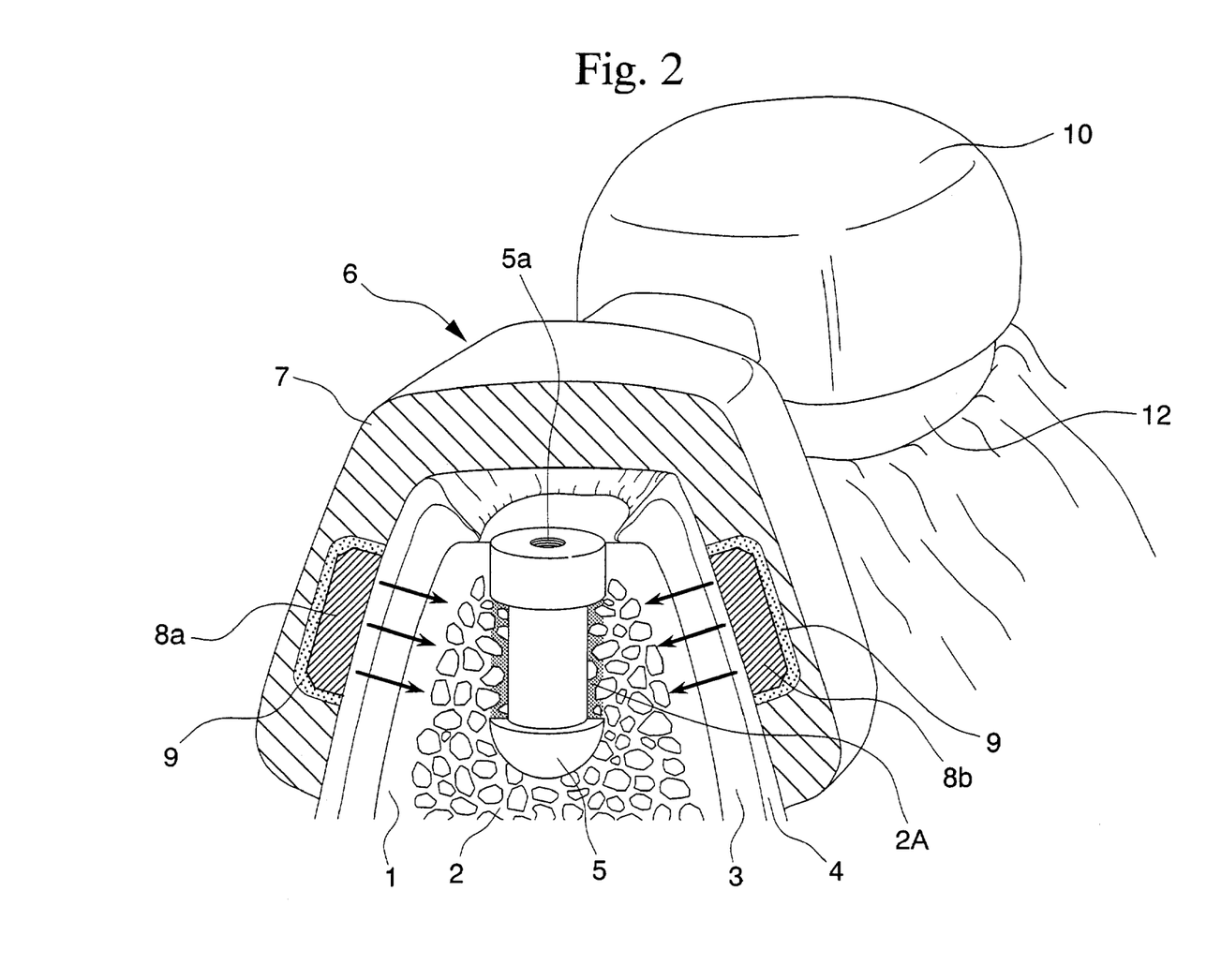
FIG. 2 is a partially exploded view of the ultrasonic therapy device of the first embodiment.

The first embodiment will be explained with reference to FIGS. 1A, 1B, and 2. FIGS. 1A and 1B show an outline of a first embodiment of the present Invention. FIG. 2 shows a partially exploded perspective view of the ultrasonic therapy device 6 in a state in which the ultrasonic device 6 is attached to a gum in an oral cavity.

In FIG. 2, the numeral 1 indicates a gum from which a tooth was extracted, the numeral 2 indicates a dentary, the numeral 3 indicates a gingival tissue and the numeral 4 indicates an epidermis. The numeral 5 indicates an implant (an implant fixture) as an artificial root which is embedded in the gum 1 into the dentary 2. A screw hole 5a to which an artificial crown is screwed is formed in an upper face of the implant 5. The numeral 2A indicates an osseous tissue which grows around the implant 5.

In FIGS. 1A, 1B, and 2, the numeral 6 indicates an ultrasonic therapy device which consists of bodies 7 which are unified and a pair of fixing frames 10 and 11. A bottom face of the body 7 is opened and a pair of oscillators 8a and 8b are embedded in an inner face of the body 7. The pair of oscillators 8a and 8b are facing each other.

One face of each of the oscillators 8a and 8b is exposed so that the oscillators 8a and 8b touch with a surface of the epidermis 4 and the other face of the oscillators 8a and 8b are covered by vibration absorbing members 9. The fixing flames 10 and 11 have a form of crown so as to cover intact teeth 12 and 13 which are located next to the implants 5 and are fixed to the body 7 by connecting portions 10a and 11a. Lead wires 14 to supply an ultrasonic signal to drive the oscillators 8a and 8b extend from the body 7. In the embodiment shown in FIG. 1A, the lead wires 14 extend out of the oral cavity.

Next, a therapy method utilizing the equipment in the first embodiment will be explained.

As shown in FIG. 1B, two implants 5 are embedded in the gum from which one tooth and another tooth which was located next to the one tooth were extracted. The bodies 7 of the ultrasonic therapy device 6 are supported between the teeth 12 and 13 and cover the gum 1 by the fixing frames 10 and 11 which cover the teeth 12 and 13. The ultrasonic therapy device 6 thus supported is securely attached to the affected area.

In this state, by supplying ultrasonic signals generated by an external ultrasonic generator (not shown in the figures) to the oscillators 8a and 8b through the lead wire 14, it is possible to accelerate a ossification in an osseous tissue 2A in the dentary 2.

It is possible to exactly fix the two bodies 7 of the ultrasonic therapy device 6 in the oral cavity by the above construction, and therefore it is possible to supply the ultrasonic signals to the oscillators which are fixed in an affected area so as to accelerate the ossification in the osseous tissue 2A. Because the oscillators 8a and 8b are supported in the body 7 with the vibration absorbing members 9 so as not to transfer the vibration out of the affected area, a patient does not feel discomfort.

A number of the bodies is not limited to two, and as explained in the above embodiment, an ultrasonic therapy device having one body and an ultrasonic therapy device having three or more bodies combined with each other are also possible.

Figure 3A:
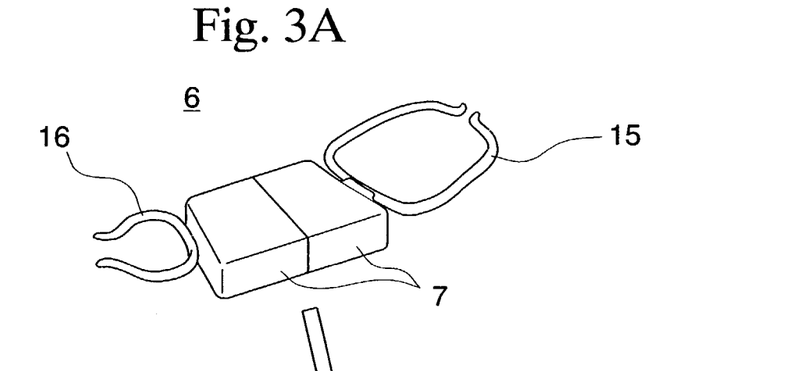
FIG. 3A is a perspective view of the second embodiment of the ultrasonic therapy device of the present Invention.
Figure 3B:
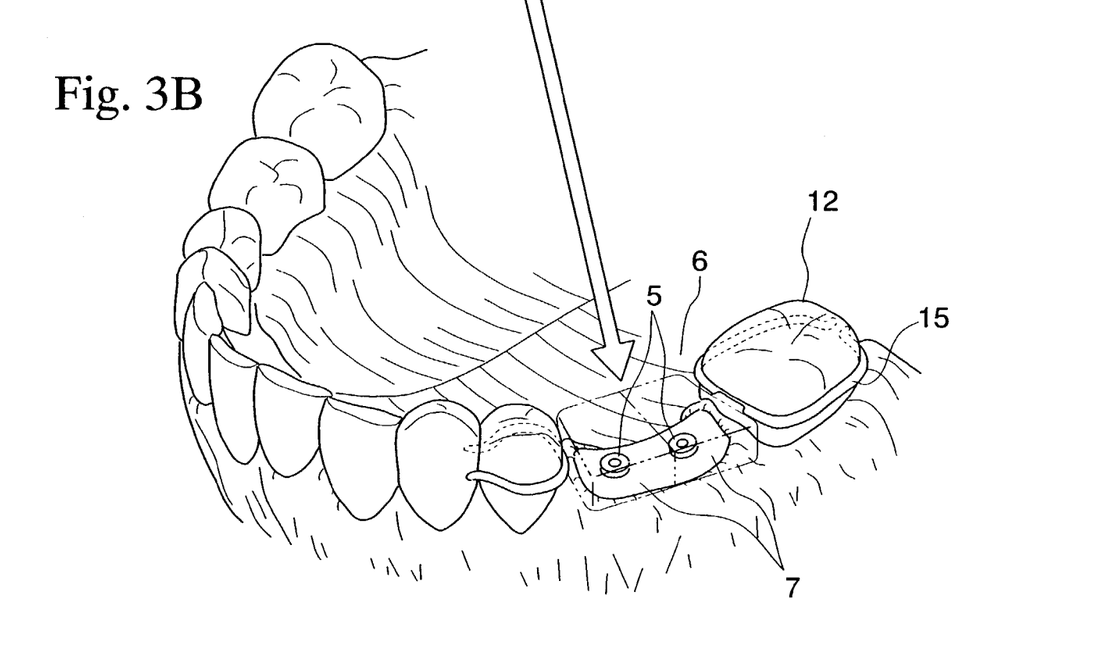
FIG. 3B is a perspective view of the second embodiment of the ultrasonic therapy device in a state in which the device is placed at an affected portion.

FIGS. 3A and 3B show the second embodiment of the present Invention. In this embodiment the same reference numerals are used for the members of the embodiment which are equivalent to those of the first embodiment, and explanations for the equivalent members are omitted.

The ultrasonic therapy device of this embodiment 6 comprises two bodies 7 which are connected to each other. Each side face of the bodies 7 comprises connecting portion 15 (16) made of a wire having a U-shape.

The above ultrasonic therapy device 6 will be placed in an affected area by the following steps.
(1) Placing the bodies 7 at the affected area into which the implants 5 are embedded.
(2) Elastically bending the connecting portions 15 and 16 and engaging the connecting portions with the teeth 12 so as to wind around the teeth 12.

By the above steps of placing, the bodies 7 of the ultrasonic therapy device 6 are securely fixed in an oral cavity.

The number of bodies is not limited to two, as explained in the above embodiment, and an ultrasonic therapy device having one body and an ultrasonic therapy device having three or more bodies combined with each other are also available.

Figure 4:
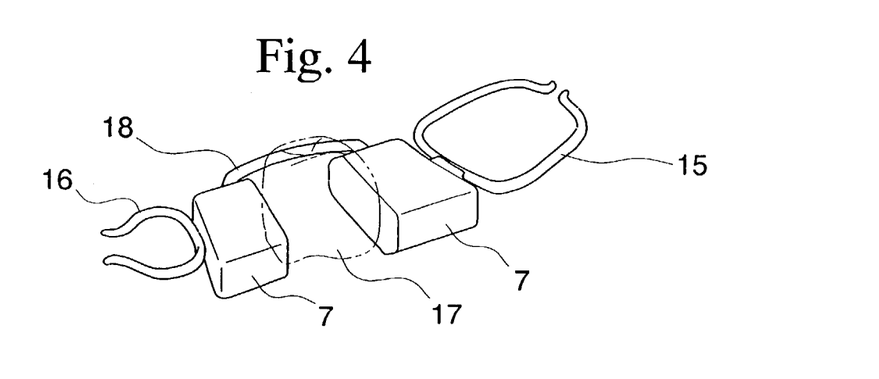
FIG. 4 is a perspective view of the third embodiment of the ultrasonic therapy device of the present Invention.

FIG. 4 is a perspective view of the third embodiment of the present Invention. In this embodiment, the same reference numerals are used for the members of the embodiment shown in FIGS. 3A and 3B which are equivalent to those of the first embodiment, and explanations for the equivalent members are omitted.

In this embodiment, two bodies 7 are connected to each other with a distance which corresponds to a size of a healthy tooth 17 which exists between affected areas by a connecting member 18 which is made by a wire having a figure corresponding to an outline of tooth to be engaged.

The ultrasonic therapy device 6 of the third embodiment is suitable for using in the affected areas between which the healthy tooth exists.

Figure 5A:
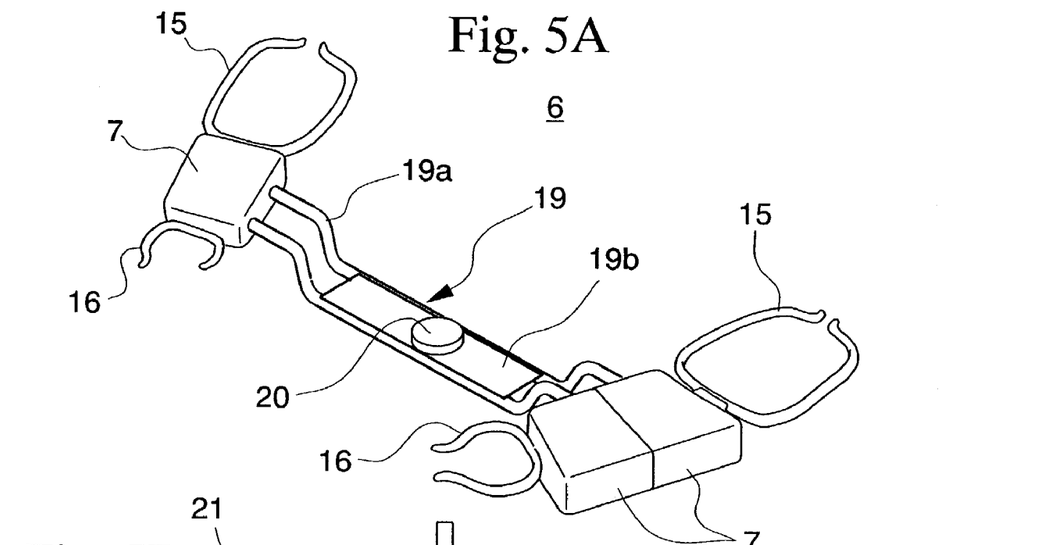
FIG. 5A is a perspective view of the fourth embodiment of the ultrasonic therapy device of the present Invention.
Figure 5B:
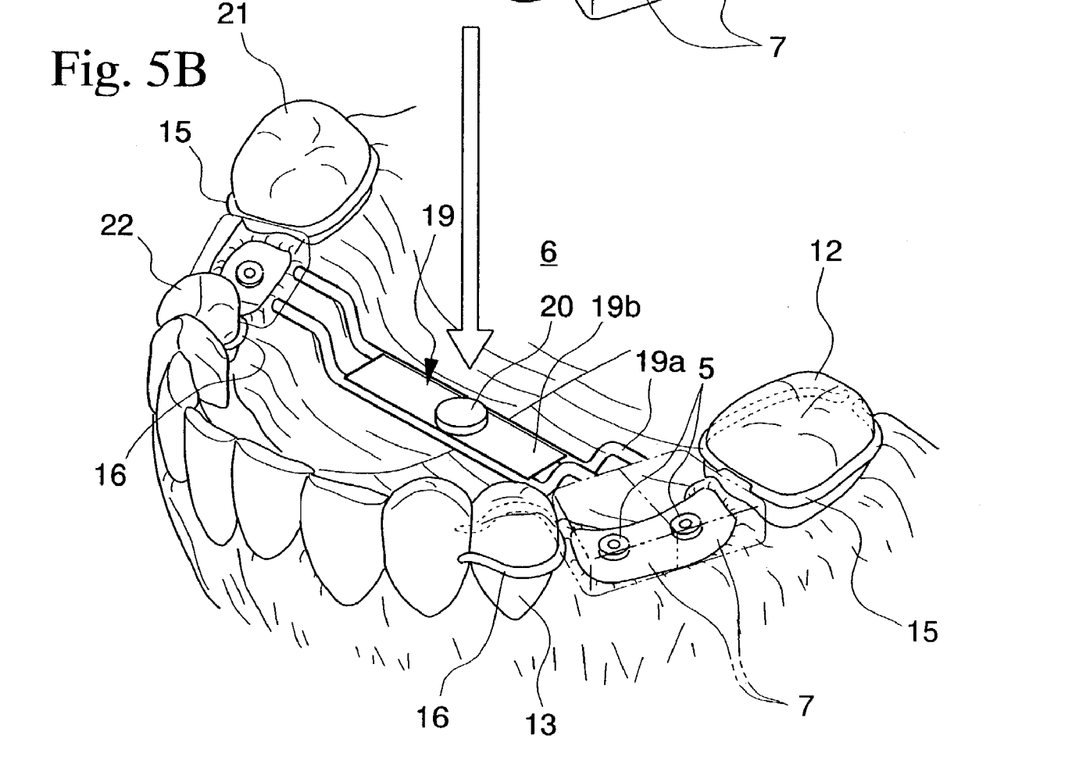
FIG. 5B is a perspective view of the fourth embodiment of the ultrasonic therapy device in a state in which the device is placed at an affected portion.

FIGS. 5A and 5B are perspective views of the fourth embodiment of the present Invention. In this embodiment the same reference numerals are used for the members of the embodiment shown in FIGS. 3A and 3B which are equivalent to those of the first embodiment, and explanations for the equivalent members are omitted.

The ultrasonic therapy device 6 of this embodiment provides the two bodies 7 and the connecting portions each of which having a construction the same as the ultrasonic therapy device shown in FIG. 3. The two bodies 7 are connected each other by a connecting member 19 which consists of a wire 19a and a plate 19b on which an oscillator 20 is mounted.

The ultrasonic therapy device shown in FIG. 1A can also be utilized for the fourth embodiment in place of the ultrasonic therapy device shown in FIG. 3A.

As shown in FIG. 5B the bodies 7 are placed between the teeth 12 and 13 and also between the teeth 21 and 22. Each of the connecting portions 15 and 16 is elastically bent and is engaged with the teeth so as to securely fix the bodies 7. In the state shown in FIG. 5B, it is possible to transmit the ultrasonic waves from the oscillator 20 to the bodies. In this embodiment, it is possible to simultaneously heal three affected teeth.

Figure 6A:
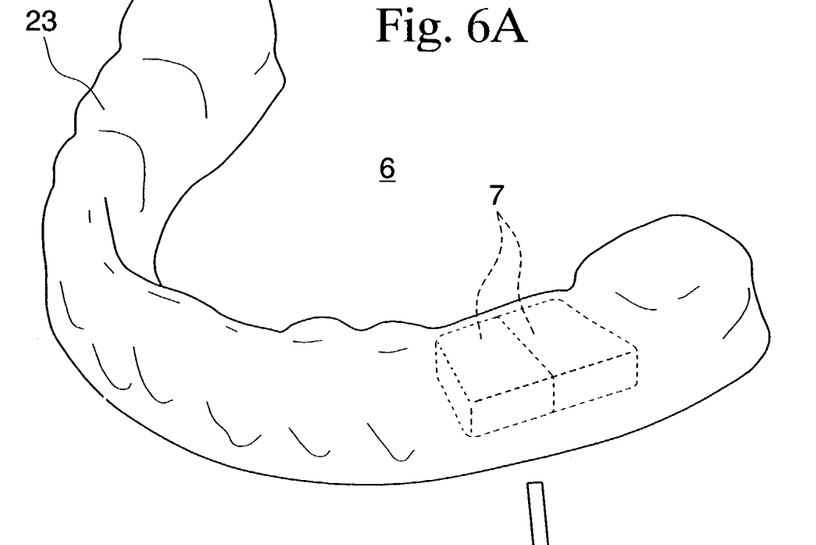
FIG. 6A is a perspective view of the fifth embodiment of the ultrasonic therapy device of the present Invention.
Figure 6B:
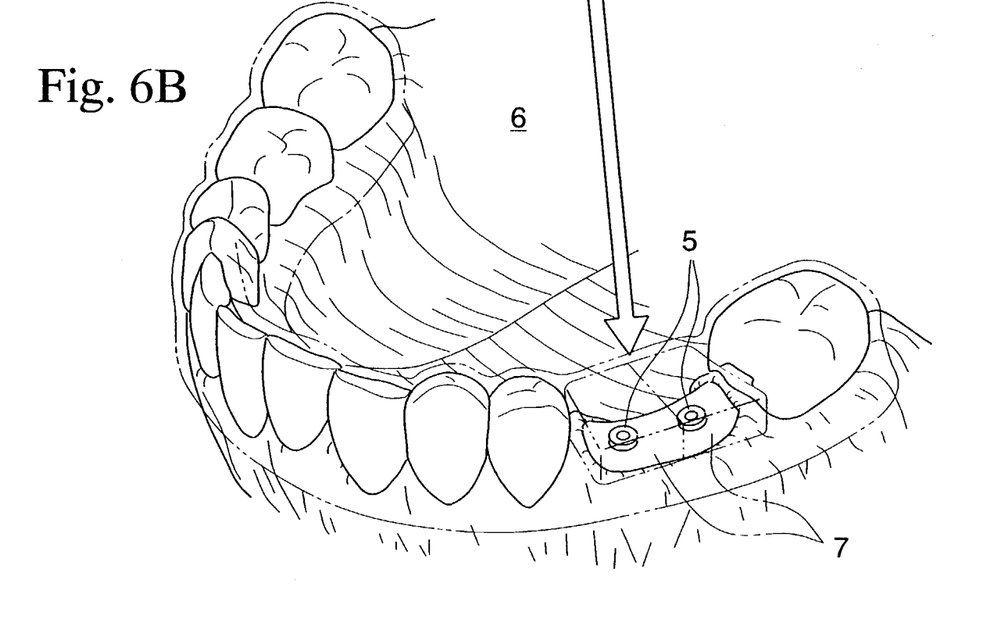
FIG. 6B is a perspective view of the fifth embodiment of the ultrasonic therapy device in a state in which the device is placed at an affected portion.

FIGS. 6A and 6B are perspective views of the fifth embodiment of the present Invention. In this embodiment, the same reference numerals are used for the members of the embodiment shown in FIGS. 1A and 1B which are equivalent to those of the first embodiment, and explanations for the equivalent members are omitted.

A supporting member 23 which covers all the teeth of the maxilla or the mandibula is utilized so as to support the ultrasonic therapy device in an oral cavity of a patient. In this embodiment two bodies 7 are arranged in the supporting member. A number of the body is not limited to, as explained in the above embodiment, and an ultrasonic therapy device having one body and an ultrasonic therapy device having three or more bodies combined together are also possible. The supporting member can be made by using a mold which corresponds to a teeth profile of a patient.

It is possible to stably support the body 7 of the ultrasonic therapy device in any position in the oral cavity of the patient by using the supporting member 23 of this embodiment.

Figure 7:
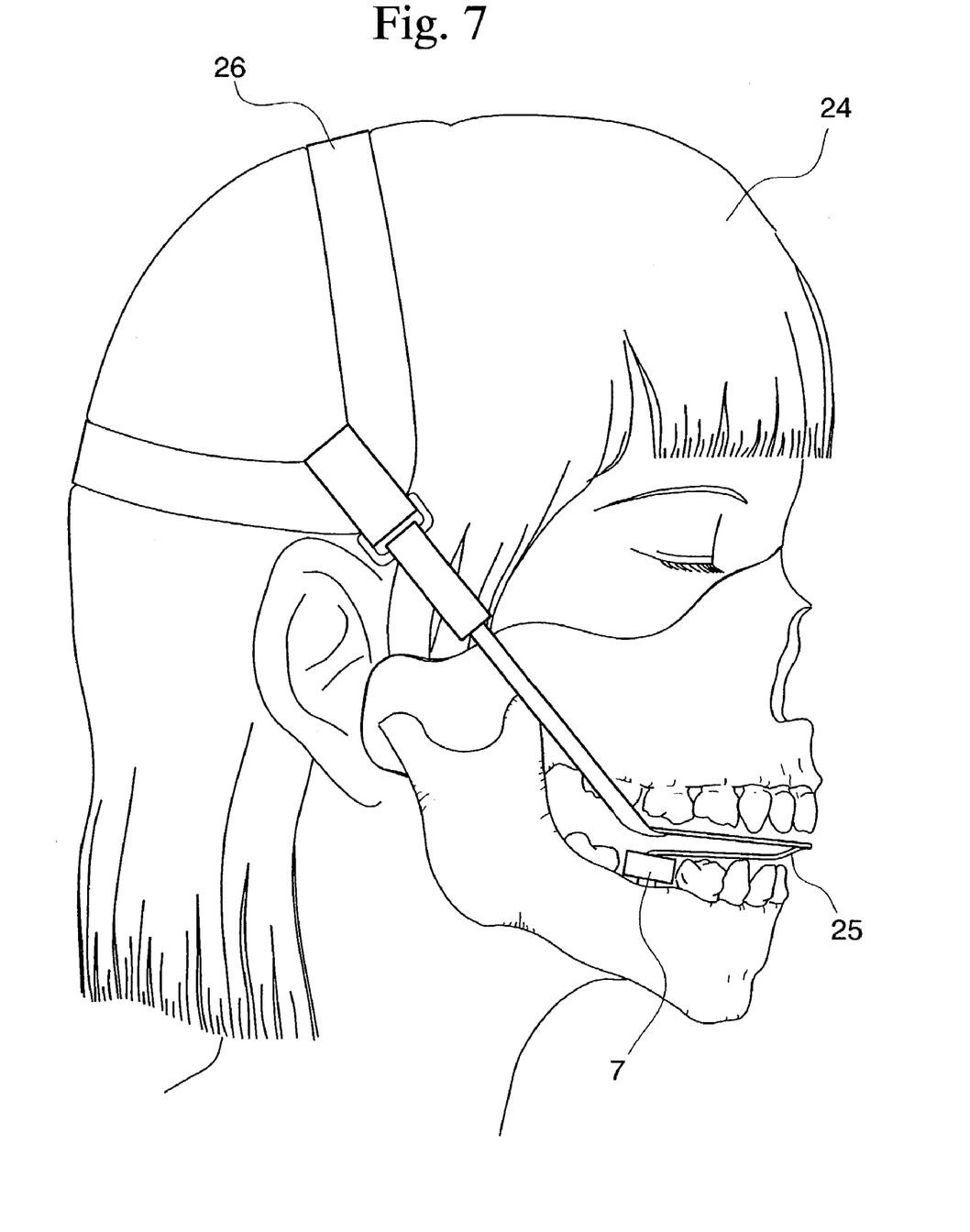
FIG. 7 is a side view of the sixth embodiment of the ultrasonic therapy device.

FIG. 7 is a side view of the sixth embodiment of the present Invention.

In FIG. 7, an affected portion of an oral cavity of a patient 24 is covered by the body 7 which is connected with one end of a spring member 25 which is made of a steel wire. The patient 24 wears a headgear 26 which supports the other end of the spring member 25. The body 7 is elastically supported by the patient 24 so as to be held in an affected portion.

Next, the seventh embodiment will be explained.

In the seventh embodiment, a supporting member to be held in a hand of a patient and having a concave form which corresponds to a convex form of the mouth of the patient is used to hold the body or the oscillator of the ultrasonic therapy device.

It is possible to support the oscillator at an affected portion of a patient by using the supporting member, and it is also possible to transmit ultrasonic waves to the affected portion.

Next, the eighth embodiment will be explained.

Figure 8:
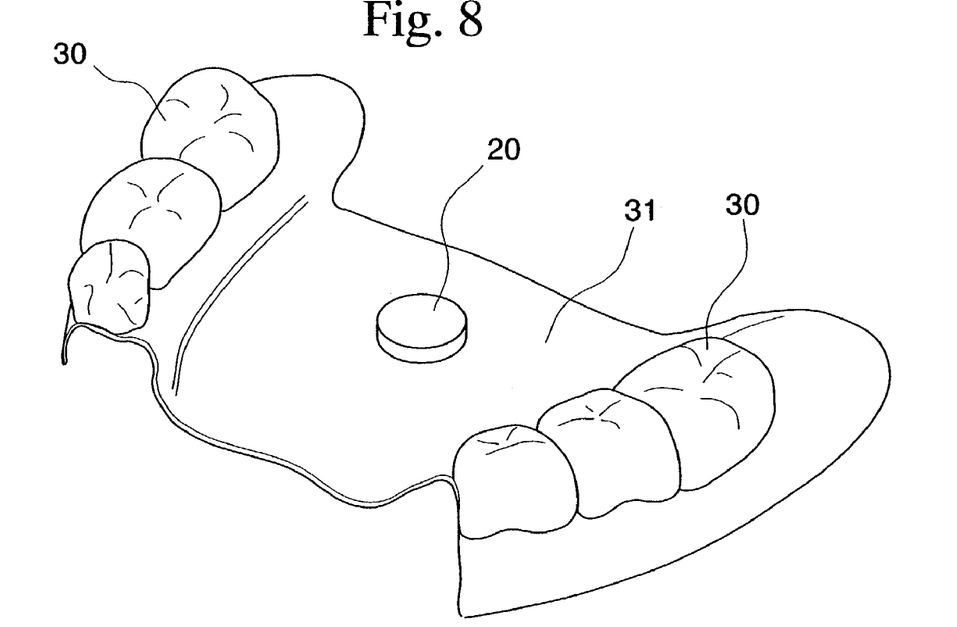
FIG. 8 is a perspective view of the eighth embodiment of the ultrasonic therapy device.

In this embodiment, the oscillator 20 is arranged in a bed member 31 which holds some dentures 30 and is supported in an oral cavity. A oscillator 20 is fixed in the bed member 31. It is possible to transmit ultrasonic waves generated by the single oscillator 20 to an affected portion under each of the dentures 30 through the bed member 31, and therefore it is possible to heal a plurality of affected portions into which implant fixtures are embedded by the single oscillator 20. It is desirable for the ultrasonic therapy device of this embodiment to be arranged with a vibration absorbing member made of an elastic material at some portions of the bed member 31 so that portions of the patient, such as the inner surface of the maxilla or the mandibula, other than the affected area to be vibrated, do not have ultrasonic waves transmitted thereto.

Next, the ninth embodiment will be explained.

Figure 9:
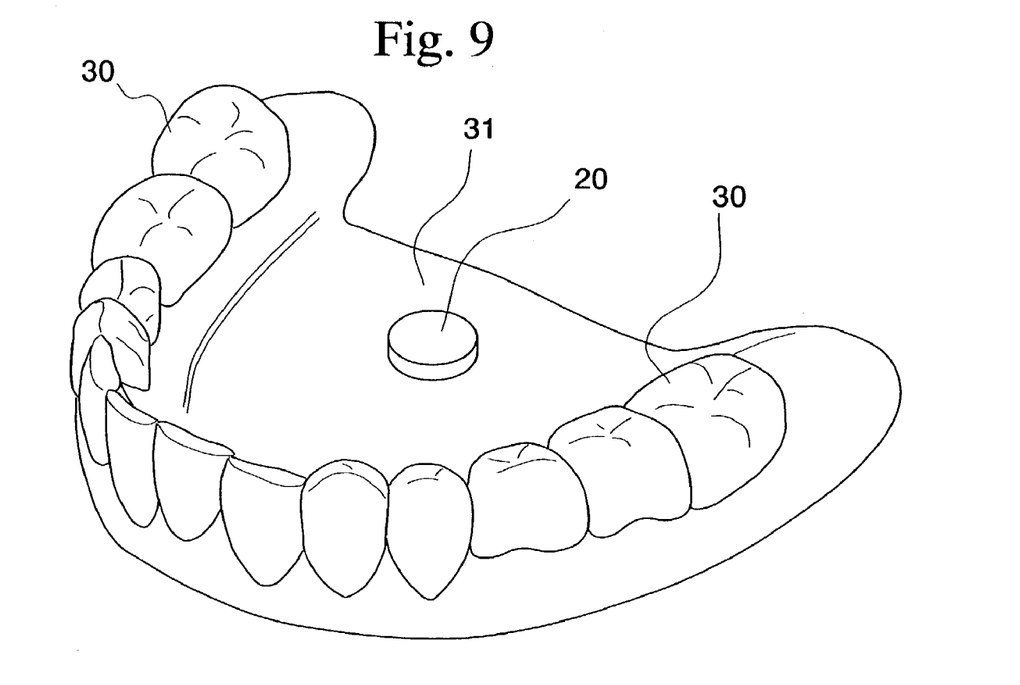
FIG. 9 is a perspective view of the ninth embodiment of the ultrasonic therapy device.

This embodiment is suitable for a patient having no tooth in the maxilla or the mandibula. Dentures 30 relative to the entire of teeth of the maxilla or the mandibula is arranged in a bed member 31. The bed member 31 will be held in an oral cavity of a patient and in which an oscillator 20 is arranged. Because ultrasonic waves generated by the oscillator 20 are transmitted to each affected portion under the dentures 30 through the bed member 31, it is possible to heal the entirety of affected portions in the maxilla or the mandibula having no teeth by using a single oscillator 20.

It is possible to arrange two or more oscillators 20 in accordance with the numbers of the affected portions so as to obtain a necessary strength of the ultrasonic waves.

It is possible for the vibration absorbing member to be arranged at faces except for portions of the oscillator which face to the affected portion. Lead wires to supply ultrasonic signal to the oscillators are arranged in the fixing member.

Next, effects due to the ultrasonic therapy devices of the above explained embodiments will be explained.

1) Accelerating osteogenesis and osteointegration around an affected portion of an implant fixture after embedding the implant fixture.
2) Accelerating osteogenesis and osteointegration around an affected portion of an implant fixture after removing the implant fixture.
3) Accelerating ostegenesis in dentary defect around an implant fixture.
4) Accelerating ostegenesis in dentary hyperplasia for a donor and a recipient
5) Accelerating ostegenesis in a technique for extension osteogenesis.
6) Accelerating postoperative healing in a maxillofacial injuries, maxillofacial fractures, and tooth dislocations.
7) Accelerating ostegenesis after surgery a maxillofacial deformity.
8) Minimizing a non-retention period and a retention period during orthodontic therapy.
9) Accelerating ostegenesis in an osteorrhaphy portion after a redressment.
10) Accelerating a secondary dentine organization after a vital pulp cutting and direct or indirect vital pulp covering in a repair of dental caries.
11) Pain reduction for a dentine hyperesthesia by accelerating a secondary dentine organization.
12) Accelerating blocking of an apical area after a removal of a vital pulp and an operation for an inflected vital pulp.
13) Accelerating recovery after a periodontal surgery. (Flap operation FGG APF)
14) Accelerating osteogenesis after a tooth fixing in an occlusal trauma.
15) Accelerating recovery for insufficient healing after surgery.
16) Accelerating recovery of abnormal frenulum after surgery.
17) Accelerating recovery after a surgery for a cheiloschisis, a palatoschisis, and a cheilognathoschisis.
18) Accelerating an osteogenesis after a surgery of ankylosis of the temporomandibular joint.
19) Accelerating osteogenesis and recovery after surgery for osteitis and osteomyelitis.
20) Accelerating a normalization for a function of sialaden.
21) Accelerating healing after an osseous nidus exenteration in an odontological maxillofacial area.
22) Accelerating osteogenesis in a periodontal osseous defect. (GTR and GBR technique)
23) Accelerating osteoatresia of a root apex during dental therapy.
24) Accelerating healing of a wound after removing a soft tissue in an odontological maxillofacial area, a soft tissue damaged by trauma, and a surgically modified soft tissue.
25) Accelerating osteogenesis of new tissue around an implanted tooth and a re-planted tooth.
26) Accelerating curing of an exodontias cavity.
27) Relieving a muscle fatigue in temporomandibular arthrosis.
28) Accelerating osteogenesis in glenmoid head and clenoid cavity in temporomandibular arthrosis.
29) Accelerating healing of a surface lesion in soft tissue.

What is claimed is:

1. An ultrasonic therapy device, comprising
at least one body which is disposable in a vicinity of an affected area where an implant fixture is embedded, an oscillator disposable in the vicinity of the affected area where the implant fixture is located for outputting ultrasonic waves to said affected area, wherein the oscillator is arranged at an inner face of the body, and a pair of holding members arranged at side faces of the body and having a form of a crown so as to cover teeth next to the affected area when the device is disposed in the vicinity of the affected area.

2. An ultrasonic therapy device comprising at least one body which is disposable in a vicinity of an affected area where an implant fixture is embedded, an oscillator disposable in the vicinity of the affected area where the implant fixture is located for outputting ultrasonic waves to said affected area, wherein the oscillator is arranged at an inner face of the body, and a pair of engaging members which are arranged at side faces of the body and adaptable to elastically engage with teeth next to the affected area so as to wind around the teeth when the device is disposed in the vicinity of the affected area.

3. An ultrasonic therapy device according to claim 1, wherein, a plurality of bodies is arranged so that one of the bodies is separated to the other of the bodies and is connected to the other of the bodies by a connecting member.

4. An ultrasonic therapy device according to claim 1, wherein a wire through which an ultrasonic signal is supplied is arranged in said oscillator.

5. An ultrasonic therapy method comprising a step of embedding an implant fixture in a patient and a step of emitting ultrasonic waves to the patient, wherein said ultrasonic waves are radiated by an ultrasonic therapy device of claim 1.

6. An ultrasonic therapy method comprising a step of embedding an implant fixture in a patient and a step of emitting ultrasonic waves to the patient, wherein said ultrasonic waves are emitted by an ultrasonic therapy device of claim 3.

* * * * *